United States Patent [19]

Standke et al.

[11] Patent Number: 6,100,418
[45] Date of Patent: Aug. 8, 2000

[54] LESSENING RESIDUAL HALOGEN CONTENT AND IMPROVING COLOR NUMBER IN ALKOXYSILANES OR ALKOXYSILANE-BASED COMPOSITIONS

[75] Inventors: Burkhard Standke, Loerrach; Jaroslaw Monkiewicz; Albert-Johannes Frings, both of Rheinfelden; Ralf Laven, Schwoerstadt; Roland Edelmann, Wehr; Peter Jenkner, Rheinfelden; Helmut Mack, Rheinfelden; Michael Horn, Rheinfelden, all of Germany

[73] Assignee: Sivento Chemie Rheinfelden GmbH, Rheinfelden, Germany

[21] Appl. No.: 09/310,145

[22] Filed: May 12, 1999

[30] Foreign Application Priority Data

May 12, 1998 [DE] Germany .......................... 198 21 156

[51] Int. Cl.$^7$ ...................................... C07F 7/08

[52] U.S. Cl. .............................................. 556/466

[58] Field of Search .............................. 556/466

[56] References Cited

U.S. PATENT DOCUMENTS

| 4,156,689 | 5/1979 | Ashby et al. | 556/451 |
|---|---|---|---|
| 4,297,500 | 10/1981 | Finke et al. | 556/466 |
| 4,661,612 | 4/1987 | George et al. | 556/450 |
| 5,210,250 | 5/1993 | Watanuki et al. | 556/466 |
| 5,777,145 | 7/1998 | Marko | 556/466 |

*Primary Examiner*—Paul F. Shaver
*Attorney, Agent, or Firm*—Oblon, Spivak, McClelland, Maier & Neustadt, P.C.

[57] ABSTRACT

The residual halogen content in alkoxysilanes and in alkoxysilane-based compositions is reduced by a process comprising, treating the alkoxysilane or the alkoxysilane-based composition with activated carbon.

15 Claims, No Drawings

LESSENING RESIDUAL HALOGEN CONTENT AND IMPROVING COLOR NUMBER IN ALKOXYSILANES OR ALKOXYSILANE-BASED COMPOSITIONS

BACKGROUND OF THE INVENTION

1. Field of the Invention

The present invention relates to a process for lessening residual halogen content in alkoxysilanes or alkoxysilane-based compositions. More particularly, the present invention relates to improving the color number of alkoxysilanes or alkoxysilane-based compositions.

2. Description of the Background

Alkoxysilanes and alkoxysilane-based compositions are employed in numerous fields: as adhesion promoters, as release agents, as crosslinkers in polymers, as additives in paints and coating materials, for the hydrophobicization of surfaces, inter alia for textiles and leather and, in particular, for the protection of buildings and facades, for book preservation, for the special modification of the properties of surfaces such as the coating of glass fibers or the silanization of fillers and pigments, and also for improving the rheological properties of polymer dispersions and emulsions, to name but a few examples.

Alkoxysilanes are normally prepared from halosilanes, especially chlorosilanes. For example, by reacting an alkyltrichlorosilane with methanol an alkyltrimethoxysilane is obtained and HCl is evolved. Even after distillative purification of the product, residual amounts of acid chloride may remain in the alkoxysilane in the order of magnitude of from around 50 to 500 ppm by weight. In the case of the preparation of, for example, aminoalkyltrialkoxysilanes by reacting chloroalkyltrialkoxysilanes with $NH_3$ or an alkylamine and then separating the ammonium chloride salt produced, which is the predominant chloride product, by filtration, residual amounts of acidic or hydrolyzable chloride remain in the product. In addition, the product may also contain residual amounts of what is known as nonhydrolyzable chlorine, for example, unreacted starting materials such as chloroalkylalkoxysilanes.

Currently, alkoxysilanes, especially oligomeric alkoxysilanes or silane systems based thereon, and products which comprise alkoxysilanes, cf. e.g. EP O 273 867 B1, DE 27 51 714 C2, and alkoxysilane-based compositions, as disclosed, for example, by EP O 049 365 A2, EP O518 057 A1, EP O 675 128 A1, EP O 716 127 A2 or EP O 716 128 A2, to name but a few, are prepared with the objective of having very low halide contents, especially of acidic or hydrolyzable chlorides.

It is known that the residual halogen content can be removed from alkoxysilanes by means, inter alia, of reaction or neutralization with alkali metal alcoholates such as sodium methanolate, and separation of the resultant salt (EP O 282 486 A2, EP O 741 137 A1). Neutralization methods of this kind are usually laborious and in general cannot be applied to stabilized alkoxysilane-based compositions.

It is also known to employ activated carbon as an adsorbent for removing, inter alia, chlorine from water (Rompp Chemie Lexikon, 9th edition, page 83, under Activated carbon and page 59 under Adsorbents).

It is also known, as disclosed in Chemical Abstracts Vol. 117 (1992), p. 713, CA 117: 251554n), to remove chloride compounds from alkyl- and arylalkoxysilanes by treatment with an alkali-treated activated carbon and basic ion exchange resins.

DE-A 28 07 589 discloses the removal of biphenyls and other impurities from impure silanes and siloxanes by bringing them into contact with a fixed bed of molecular sieves and carbon.

U.S. Pat. No. 5,567,836 discloses a process in which methyltrichlorosilane is separated from dimethyldichlorosilane using activated carbon.

A need continues to exist for improvements in the preparation of high purity alkoxysilanes.

SUMMARY OF THE INVENTION

Accordingly, one object of the present invention is to provide an effective method of preparing alkoxysilanes and alkoxysilane-based compositions of high purity, low residual chlorine content in a simple and economic manner.

Briefly, this object and other objects of the present invention as hereinafter will become more readily apparent can be attained by a process for decreasing the residual halogen content of alkoxysilanes and alkoxysilane-based compositions which comprises treating the alkoxysilane or the alkoxysilane-based composition with activated carbon.

DETAILED DESCRIPTION OF THE PREFERRED EMBODIMENTS

It has now been surprisingly found that it is possible in a simple and economic manner to achieve virtually quantitative removal of residual acidic or hydrolyzable chloride contents from alkoxysilanes or from alkoxysilane-based compositions by treatment of these substances with activated carbon. Examples of these materials include aqueous solutions of silane hydrolyzates or silane condensates in which case solvents, for example, alcohols such as methanol, ethanol, isopropanol and 2-methoxyethanol, or water or aliphatic hydrocarbons such as hexane, heptane and isomer mixtures and mixtures of aliphatic hydrocarbons may also be present.

It has also been found that the activated carbon treatment of the invention makes it possible advantageously not only to reduce the content of hydrolyzable chloride down to residual amounts, but also to reduce by a more than proportionate amount the content of total chloride in the product.

Moreover, when using activated carbon in the present process, it has also been found, advantageously and surprisingly, that a simultaneous improvement in the color number of treated alkoxysilanes and alkoxysilane-based compositions is achieved.

The halides which are normally present in the alkoxysilane product are in particular the so-called hydrolyzable and/or nonhydrolyzable chlorine compounds.

In general, the treatment of alkoxysilanes or alkoxysilane-based compositions by the present process is effected by bringing the alkoxysilane or the alkoxysilane-based composition into contact with activated carbon, with or without stirring, and allowing the materials to react with carbon.

Treatment of the alkoxysilane or alkoxysilane-based composition is suitably conducted within a temperature range ranging from 0 to 200° C., preferably from 10 to 100° C., and more preferably from 20 to 80° C.

It is normally advantageous to effect this treatment over a time of 1 minute to 8 hours, preferably from 2 minutes to 1 hour and, particularly from 5 to 20 minutes, normally with thorough mixing of the materials.

In general, the activated carbon is subsequently separated from the alkoxysilane or from the treated composition by means of, for example, filtration.

In the process of the invention it is preferred to employ an activated carbon which is in powder form and which has been obtained from peat and activated with steam. The activated carbon preferably used in the method of the invention has an average bulk density of 520 g/l, an average pore surface area (BET) of 600 m²/g and a pH of from 6.5 to 7.5. Suitably, 80% by weight of the particles are on average smaller than 10 μm, i.e. 80% by weight of the activated carbon employed preferably has a particle size of from 0.01 to 10 μm. Such product parameters are possessed, for example, by the activated carbon identified as NORIt® PN 5.

The process of the invention can be applied, for example, but not exclusively, to the following alkoxysilanes or alkoxysilane-based compositions: vinyltrimethoxysilane, vinyltriethoxysilane, vinyltris(2-methoxyethoxy)silane, vinylmethyldimethoxysilane, 3-aminopropyltrimethoxysilane, 3-aminopropyltriethoxysilane, N-aminoethyl-3-aminopropyltrimethoxysilane and also triamino-functional propyltrimethoxysilanes and technical grades of said alkoxysilanes, as well as compositions of oligomeric organoalkoxysiloxanes, examples being oligomeric vinylsiloxanes, such as DYNASYLAN® 6490 which is prepared, starting from vinyltrimethoxysilane, by targeted condensation, or DYNASYLAN® 6498, which may be obtained by targeted condensation starting from vinyltriethoxysilane, and also compositions with oligomeric vinyl/alkylsiloxanes such as DYNASYLAN® 6598, as revealed in particular by EP 0 518 957 A1, and also compositions with oligomeric alkylalkoxysilanes such as DYNASYLAN® 9281, cf. DE 196 24 032 A1, and compositions of water-soluble, predominantly fully hydrolyzed organopolysiloxanes, as disclosed particularly in EP 0 675 128 A1, EP 0 716 127 A2 and EP 0 716 128 A2.

With the process of the invention, the content of acidic chlorides in an alkoxysilane can suitably be reduced, for example, from around 500 ppm by weight to<10 ppm by weight, preferably to≦3 ppm by weight, i.e. suitably down to the detection limit.

It is also possible, when employing the process of the invention, to reduce the total chlorine content in alkoxysilanes or in alkoxysilane-based compositions such as a water-containing and vinyltriethoxysilane-methyltriethoxysilane condensate-based compositions, from, for example, 330 ppm by weight to 45 ppm by weight, it being possible to reduce the proportion of hydrolyzable chloride in a simple and economic manner from 17 ppm by weight to≦3 ppm by weight.

In particular, the use of the process of the invention also makes it possible in an advantageous and surprising way to achieve an improvement in the color number (APHA in accordance with DIN ISO 6271) of alkoxysilanes and alkoxysilane-based compositions.

The present invention also provides a process for reducing the residual halogen content and/or simultaneously or independently improving the APHA color number of alkoxysilanes and alkoxysilane-based compositions by treating the alkoxysilane or alkoxysilane-based composition with activated carbon.

Having now generally described the invention, a further understanding can be obtained by reference to certain specific Examples which are provided herein for purpose of illustration only and are not intended to be limiting unless otherwise specified.

EXAMPLE 1

A 826 g amount of a reaction mixture obtained from the preparation of a vinyl-n-propylsilane cocondensate and following the removal of low-boiling constituents such as ethanol is heated to 40° C. in a round-bottom flask, and 7.5 g of NORIT® PN 5 activated carbon are added. The amount of activated carbon corresponds to an addition of 0.9 wt. % based on the reaction mixture. The product to which activated carbon has been added is stirred at 40° C. for 15 minutes. The activated carbon is subsequently removed by filtration from the vinyl-n-propylsilane cocondensate using a pressure filter. Both the hydrolyzable chloride and the total chloride in both the end product and in the reaction mixture prior to the addition of activated carbon are assayed. The Table below shows the results of these analyses:

|  | Hydrolyzable chloride | Total chloride |
| --- | --- | --- |
| Before adding activated carbon | 20 mg/kg | 60 mg/kg |
| After adding activated carbon | ≦3 mg/kg | ≦35 mg/kg |
| Detection limits | 3 mg/kg | 35 mg/kg |

A further advantage of the present process is the concomitant reduction in color number from 65 APHA to<5 APHA.

EXAMPLE 2

A 905 g amount of a reaction mixture obtained from the preparation of a vinylmethylsilane cocondensate and following the removal of low-boiling constituents such as ethanol is heated to 45° C. in a round-bottom flask, and 10.0 g of NORIT® PN 5 activated carbon are added. The amount of activated carbon corresponds to an addition of 1.1% based on the reaction mixture. The product to which activated carbon has been added is stirred at 45° C. for 10 minutes. The activated carbon is subsequently removed by filtration from the vinylmethylsilane cocondensate using a pressure filter. Both the hydrolyzable chloride and the total chloride in both the end product and in the reaction mixture prior to the addition of activated carbon are assayed. The table below shows the results of these analyses:

|  | Hydrolyzable chloride | Total chloride |
| --- | --- | --- |
| Before adding activated carbon | 17 mg/kg | 330 mg/kg |
| After adding activated carbon | ≦3 mg/kg | 45 mg/kg |
| Detection limits | 3 mg/kg | 35 mg/kg |

Here again, advantageously, a reduction in color number was observed: from 110 APHA to 10 APHA.

The disclosure of German priority Application No. 19821156.2 filed May 12, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by letters patent is:

1. A process for reducing the residual halogen content in alkoxysilanes and in alkoxysilane-based compositions, which comprises:

treating the alkoxysilane or the alkoxysilane-based composition with activated carbon.

2. The process as claimed in claim 1, wherein the activated carbon treatment is conducted at a temperature in the range from 0 to 200° C.

3. The process as claimed in claim 2, wherein the activated carbon treatment is conducted at a temperature in the range from 10 to 100° C.

4. The process as claimed in claim 1, wherein the activated carbon treatment is conducted for a period of from 1 minute to 8 hours.

5. The process as claimed in claim 4, wherein the activated carbon treatment is conducted for a period of from 2 minutes to 1 hour.

6. A process as claimed in claim 1, wherein the residual halogen content is reduced by more than 30%.

7. The process as claimed in claim 1, wherein the residual content of acidic halide is reduced to less than 10 ppm by weight.

8. The process as claimed in claim 1, wherein the halogen is chlorine.

9. The process as claimed in claim 1, wherein a solvent is present at the implementation of the activated carbon treatment.

10. The process as claimed in claim 1, wherein the activated carbon has an average bulk density of 520 g/l, an average pore surface area (BET) of 600 m$^2$/g and a pH of 6.5 to 7.5.

11. The process as claimed in claim 1, wherein 80 wt. % of the particles of the activated carbon have a size less than 10 µm.

12. The process as claimed in claim 1, wherein said alkoxysilane is vinyltrimethoxysilane, vinyltriethoxysilane, vinyltris(2-methoxyethoxy)silane, vinylmethyldimethoxysilane, 3-aminopropyltrimethoxysilane, 3-aminopropyltriethoxysilane, N-aminoethyl-3-aminopropyltrimethoxysilane, a triamino-functional propyltrimethoxysilane, a technical grade of said alkoxysilane or an oligomeric organoalkoxysiloxane.

13. The process as claimed in claim 1, wherein the acid chloride content of said alkoxysilane is reduced to <10 ppm by weight.

14. The process as claimed in claim 13, wherein the acid chloride content of said alkoxysilane is reduced to ≦3 ppm by weight.

15. A process for reducing the residual halogen content and/or improving the color number of alkoxysilanes or alkoxysilane-based compositions, which comprises:

treating said alkoxysilane or alkoxysilane-based composition with activated carbon.

* * * * *